United States Patent [19]

Ehret

[11] Patent Number: 4,710,184
[45] Date of Patent: Dec. 1, 1987

[54] ABSORBING MATERIAL CONTAINING AN ISOTHIAZOLINE-ONE-3 DERIVATIVE, APPLICATION TO PERSONAL HYGIENE AND PROCESS FOR MANUFACTURING THIS MATERIAL

[75] Inventor: Philippe Ehret, Colmar, France
[73] Assignee: Beghin-Say S.A., Thumeries, France
[21] Appl. No.: 689,043
[22] PCT Filed: Mar. 20, 1984
[86] PCT No.: PCT/FR84/00074
§ 371 Date: Nov. 23, 1984
§ 102(e) Date: Nov. 23, 1984
[87] PCT Pub. No.: WO84/03631
PCT Pub. Date: Sep. 27, 1984

[30] Foreign Application Priority Data

Mar. 23, 1983 [FR] France .................................. 83 04785

[51] Int. Cl.$^4$ ............................................. A61F 13/16
[52] U.S. Cl. ...................................... 604/368; 604/265
[58] Field of Search ............... 604/359, 360, 368, 265; 548/213, 214, 372

[56] References Cited

U.S. PATENT DOCUMENTS

| | | | |
|---|---|---|---|
| 3,562,283 | 2/1971 | Lewis et al. | 548/213 |
| 4,062,859 | 12/1977 | Weiler et al. | 548/213 |
| 4,169,949 | 10/1979 | Weiler | 548/213 |
| 4,243,703 | 1/1981 | Lewis et al. | 514/372 |
| 4,281,136 | 7/1981 | Virgilio et al. | 548/213 |
| 4,302,240 | 11/1981 | Miller et al. | 548/213 |
| 4,325,201 | 4/1982 | Lewis et al. | 514/372 |
| 4,328,347 | 5/1982 | Virgilio et al. | 548/213 |
| 4,460,642 | 7/1984 | Eriede et al. | 604/372 |
| 4,508,908 | 4/1985 | Virgilio et al. | 548/214 |
| 4,542,169 | 9/1985 | Costerton | 604/265 |
| 4,552,752 | 11/1985 | Amick | 424/21 |

FOREIGN PATENT DOCUMENTS 0722629  1/1955  United Kingdom ................ 604/360

*Primary Examiner*—John D. Yasko
*Assistant Examiner*—Jerome R. Smith, Jr.
*Attorney, Agent, or Firm*—A. W. Breiner

[57] ABSTRACT

The invention relates to personal hygiene. Its object is an absorbing material consisting of a water-insoluble hydrocolloidal polyelectrolyte absorbing a liquid several times its own weight, and of an isothiazoline-one-3 derivative.

Preferably, this absorbing material also includes a transition-metal salt and the isothiazoline-one-3 derivative obeys the general formula:

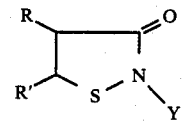

where:
R is a hydrogen atom or a $C_1$ to $C_4$ alkyl group,
R' is a hydrogen atom or a $C_1$ to $C_4$ alkyl group or a halogen,
Y is a hydrogen atom or a $C_1$ to $C_4$ alkyl group.

The invention applies to using these absorbing materials in the manufacture of disposable personal-hygiene articles.

12 Claims, No Drawings

ABSORBING MATERIAL CONTAINING AN ISOTHIAZOLINE-ONE-3 DERIVATIVE, APPLICATION TO PERSONAL HYGIENE AND PROCESS FOR MANUFACTURING THIS MATERIAL

The invention relates mainly to the field of personal hygiene.

Its object is an absorbing material consisting of a water-insoluble hydrocolloidal polyelectrolyte which absorbs an aqueous liquid several times its own weight.

Another object is the application of this material and a manufacturing process for it.

STATE OF THE ART

It is known that urine is originally sterile (except for urinary infection) but contaminated the moment it leaves the urethra by the perineal flora accommodating a large number of bacteria of which 80% consist of: proteus (50%), klebsiella, pseudomonas, coli. Furthermore, the urine represents an excellent growth substrate for these germs.

Again, menstrual blood, which contains proteins, various amines and lipids, also is a culture medium for the above-cited bacteria.

Thus, thanks to the ureases of certain bacteria, such as proteus and klebsiella, urea is transformed into ammonia in the reaction below:

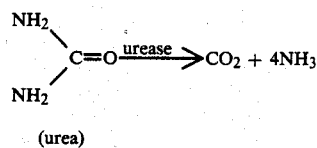

(urea)

The amino acids constituting the proteins also undergo a degradation resulting in the formation of ammonia.

Other bodies, such as the blood lipids, also are transformed into other degradation products as shown below:

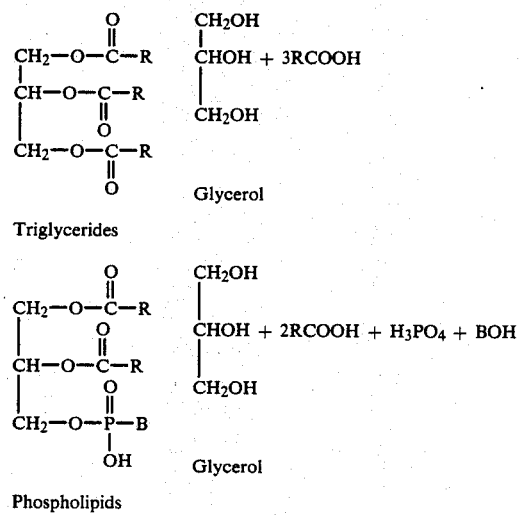

R = fatty acid derivatives
B = amino alcohol function

Illustrative fatty acids formed are butyric acid, isobutyric, and isovaleric acids.

All these reactions resulting from bacterial activity are characterized by resulting into compounds of a highly unpleasant odor.

As regards individuals with urinary and/or fecal incontinence and menstruating women, this perineal flora is directly in contact with the body fluids absorbed by the absorbing pad whereby the bad odors are formed from the action of the bacteria on these fluids. While possibly just tolerable for a baby, this phenomenon is psychologically hard to bear for an adult.

To eliminate this drawback, it has already been suggested to make use of a bactericidal substance in the absorbing pads of menstrual napkins and diapers.

Thus, French Pat. No. 2,490,093 (Landstingens Inkopscentral Lic Ekonomisk Forening) describes the incorporation, preferably at the surface, of a water-soluble copper salt in an absorbing pad consisting of cellulose fibers. In its ionic form, copper is known for its bactericidal and fungicidal properties.

This procedure, however, entails certain drawbacks. The bactericide deposited on the pad attacks the user's skin; this may lead to certain roughness and breaks in the skin, and it may even weaken the natural defenses.

Furthermore, the industrial implementation of that process is beset by certain difficulties as it is necessary to treat the entire pad surface.

Moreover, the deposition procedures (powdering, subpowdering) amount to a more than trivial danger to the personnel.

The European patent application No. 0 019 371 (Unilever) suggests incorporating a transition-metal ion (such as of copper or zinc) into an improved retention additive (IRA) which, as denoted by its name, is a body incorporated into the absorbing pad in order to improve its absorption capacity. An ion bond is set up between the anion groups (in particular COO) and the transition-metal ion. This bond is sufficiently unstable to allow the transition-metal ion to migrate out of the IRA and into the pad, and to induce the large proteins to coagulate. However, in order to achieve this migration of ions out of the IRA, it is necessary to incorporate them in relatively large amounts as about 80% of the COOH are neutralized. This represents a drawback in that the rapidity of gelling of the IRA is limited and its absorption capacity is lowered.

It is known, furthermore, that transition metals such as copper or zinc are bactericidal, and hence toxic, and that toxicologically speaking they should preferably be present in very low doses.

The object of the invention is to offer superabsorbant with bacterial activity that can be transmitted to its environment consisting of the absorbing pad. One obtains thereby the advantage of eliminating the chance of skin irritation before the arrival of the nutrient liquid.

In present-day language, the expression "superabsorbent" is synonymous with improved retention additive or with material absorbing several times its own weight in liquids.

GENERAL DESCRIPTION OF THE INVENTION

The invention is characterized in that the absorbing material includes at least one isothiazoline-one-3 derivative of the general formula:

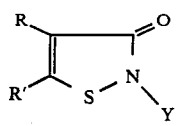

where:
  Y is a hydrogen atom, a linear or branched $C_1$ to $C_8$ alkyl group, a $C_3$ to $C_6$ cycloalkyl group,
  R is a hydrogen atom, a $C_1$ to $C_4$ alkyl group or a halogen,
  R' is a hydrogen atom, a $C_1$ to $C_4$ alkyl group or a halogen.

As regards its application, the invention is characterized in that the absorbing material is used as an improved retention additive incorporated into absorbing pads for personal hygiene, in particular for diapers for babies or incontinent adults, or for menstrual protection.

As regards the manufacturing process of the material, the invention is characterized in that first at least one isothiazoline-one-3 derivative is added to a mixture of water and alcohol and then the hydrocolloidal polyelectrolyte, whereupon the mixture will be filtered.

Hydrocolloidal Polyelectrolytes

The water-insoluble hydrocolloidal polyelectrolytes absorbing several times their own weight of aqueous liquids can be divided into two large types, namely the natural polyelectrolytes on one hand and the synthetic polyelectrolytes on the other (in particular see U.S. Pat. No. 4,043,952).

(1) The natural polyelectrolytes advantageously are selected from the anionic derivatives of starch or cellulose or dextrane also called polysaccharides. Illustrative anionic groups are the phosphate, sulfate, sulfonate, or carboxyl groups. Preferred anionic groups are the carboxylalkyl groups, and in particular the carboxyethyl and carboxymethyl groups. Preferably, the anionic groups are neutralized employing an alkaline cation such as sodium or by a primary, secondary or tertiary amine in a proportion in excess of 40% with respect to the total number of ionic groups and preferably between 40 and 85%. As a result, and in a manner known per se, the absorption capacity of the polymers will be improved. These polyelectrolytes are crosslinked so as to render them water insoluble, but obviously without changing their absorption capacity. This crosslinking may result from forming covalent bonds by esterification or etherification implemented by diols, dihalides, epichlorhydrins as in European Patent No. 0 019 371 (Unilever NV). Again crosslinking may be achieved using transition metals of the following groups in the periodic table: III B, IV B, V B, VI B, VII B, VIII B, III A, IV A, V A, VI A. Included among them are aluminum, zirconium, chromium, titanium, zinc.

(2) The homopolymers or copolymers of unsaturated carboxylic acids such as the methacrylic or polyacrylic acids (in particular see U.S. Pat. No. 4,043,952) or the homopolymers or copolymers containing sulfonic acids such as those obtained by polymerization of unsaturated sulfonic acids. These homopolymers or copolymers also are in anionic form, whether totally or partially, and are crosslinked by the same means as described in (1). The preferred polymers are those including the carboxyl groups and especially the polymethacrylic or polyacrylic acid.

All these polymers absorb between five-fold and several hundred-fold their own weight of aqueous liquid, whether it be water, urine, blood, including menstrual blood.

Illustratively, methods such as described in German Pat. No. 2,702,781 or French Pat. No. 2,305,452 may be used to determine the degree of absorption.

Another important parameter relating to these polymers is their gelling rate. A good polymer must offer the least possible gelling time, for instance by the Vortex test (G. Goldstein & M. Pierre, Marketing Technology Service Insight 81, Section IX-1-18, Publication Miller Freeman).

Isothiazoline-one-3 Derivative

The derivatives described by the general formula are known per se, and so are their bactericidal activity.

The patentability of the invention is not in this already known biocidal activity, but in the capability of these compounds to migrate outside the hydrocolloidal polyelectrolyte and to interfere with, if not prevent, the spread of the bacteria through the entire absorbing pad and thus to prevent formation of bad odors.

The following patents describe those derivatives and their preparation process:
  French Pat. No. 2,139,421 which contains an exhaustive list of the isothiazoline-one-3 derivatives;
  U.S. Pat. No. 3,517,022 which describes the preparation and the biocidal properties of the isothiazoline-one-3 derivatives;
  and also U.S. Pat. Nos. 3,544,480; 3,761,488; French Pat. No. 2,398,505.

Among the derivatives of the general formula, those will be preferred where, within the formula:
  Y is a hydrogen atom of a $C_1$ to $C_4$ alkyl group
  R is a hydrogen atom of a $C_1$ to $C_4$ alkyl group
  R' is the same as before
and, preferably too, those of a general formula wherein:
  Y is a methyl group
  R is a hydrogen atom
  R' is a hydrogen atom or a halogen or a methyl group.

In particular, the halogen can be chlorine or bromine. In order to achieve improved bactericidal activity while keeping the migratory properties of such derivatives, preferably the absorbing material includes at least two derivatives, one (A) obeying the general formula wherein R' is a halogen, such as chlorine, and preferably of the following formula:

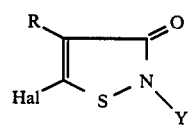

R being a hydrogen atom or a $C_1$ to $C_4$ alkyl group,
Y being a hydrogen atom or a $C_1$ to $C_4$ alkyl group,
Hal preferably being chlorine.

While the other (B) obeys the general formula wherein R' is a hydrogen atom, a $C_1$ to $C_4$ alkyl group, and preferably of the following formula:

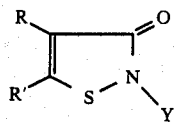

R' being a hydrogen atom or a $C_1$ to $C_4$ alkyl group,
Y being a hydrogen atom or a $C_1$ to $C_4$ alkyl group,
R being a hydrogen atom or a $C_1$ to $C_4$ alkyl group.

Preferably the absorbing material includes the two following derivatives:

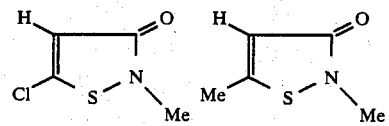

which are known by the official designations below:
A—chloro-5-methyl-2-isothiazoline-one-3
B—methyl-5-methyl-2-isothiazoline-one-3

The mixture of these products is sold by the American firm of Rohm & Haas under the brand name KATHON C.G. ® which contains about 1.5% of the isothiazoline-one-3 derivatives (1.2% of A and 0.3% of B) and 98.5% of inert material by weight.

Preferably, as regards the absorbing materials containing the (A) and (B) derivatives, the molar ratio of these two compounds is between 0.5 and 8.

Even though it is possible to incorporate the isothiazoline-one-3 derivative over a wide range of proportion by weight with respect to the polyelectrolyte without thereby transcending the scope of the invention, preferably the absorbing material shall contain a proportion by weight of the isothiazoline-one-3 derivative with respect to the polyelectrolyte which is between 1.5 and 750 ppm and better yet between 7.5 and 450 ppm, and best between 10.5 and 150 ppm.

As already described above and as is significant in the invention, the isothiazoline-one-3 derivatives migrate outside the polyelectrolyte. It was found it is entirely feasible and even desirable that the material also includes a transition metal known for its coagulating and bactericidal properties, preferably copper or zinc.

These ions can be present as halides or as organic salts. A description and an exhaustive listing will be found in French Pat. No. 2,490,093.

Halides, however, are preferred.

Surprisingly, this allows reducing the amount of the isothiazoline-one-3 derivative which is required, a highly significant development with regard to toxicology; and, furthermore, whereas the isothiazoline-one-3 derivative migrates, the metal ion remains within the polymer whereby further improvement in bactericidal coverage is assured. Additionally, the gelling rate is increased.

Preferably, the ratio by weight of the isothiazoline-one-3 derivative to the salt of a transition metal shall be between 0.012 and 0.018.

When these absorbing materials of the invention are spread in the form of grains or powder in the absorbing pads in known proportions to achieve adequate absorption, they will eliminate the odors of which the origin was discussed in the preamble.

The absorbing material of the invention is prepared at room temperature preferably using a mixture of water/methanol or water/ethanol in proportions between 80/20 and 90/10.

When the absorbing material includes a salt of a metal ion, it will preferably be incorporated before the isothiazoline-one-3 derivative.

The absorbing material is inserted in known manner into the pad in several ways, among which:
  continuous or discontinuous deposition between two plies of fluff (defibered cellulose). A particularly interesting variation of this procedure is illustrated in patent application PCT No. 79100120.
  mixing with the fluff. This fluff then is sandwiched between sheets of cotton wool or non-woven material.

EXAMPLES

All tests were performed with the isothiazoline-one-3 compounds obtained by mixing the two derivatives below:
A—chloro-5-methyl-2-isothiazoline-one-3
B—methyl-5-methyl-2-isothiazoline-one-3
(KATHON C.G. by Rohm & Haas).

EXAMPLE 1

Generalized Process For Making Absorbing Material Containing KATHON C.G. and Copper in Ionic Form The metal ion in the form of cupric chloride is added to a mixture (80/20) of methanol/water, next KATHON C.G., and lastly the polyelectrolyte are added.

The proportions by weight are as follows:

| | |
|---|---|
| polyelectrolyte | 100 |
| KATHON C.G. | 1.5 |
| $CuCl_2$ | 3 |

Following filtration, the polymer powder associated with the other two compounds is recovered. The methanol is recycled.

EXAMPLE 2

Gelling Rate

The three polyelectrolytes below were tested:
A—polycarboxyl starch known as the SANWET brand of the Sanyo company.
B—an alkaline metal polyacrylate known as the AQUAKEEP brand of the Seiteettsu company.
C—carboxymethyl starch known as the AKUCELL brand of the Akzo company.

Carrying out the so-called Vortex test (see description of the polyelectrolytes), the following results are obtained concerning the gelling rates (in seconds):

| | Urine 100 cc | Blood 100 cc |
|---|---|---|
| 2 g of B | 3" | 26" |
| with KATHON C.G. + $Cu^{++}$ | 2.5" | 19" |
| 4 g of C | 19" | 120" |
| with KATHON C.G. + $Cu^{++}$ | 16.5" | 57" |

This shows in very surprising manner that the presence of the two bactericidal compounds substantially improves the gelling rate.

EXAMPLE 3

Migration of the Bactericides

By Zone Inhibition

A certain amount of the product to be tested is deposited on paper disks which are placed on agar seeded with a specific microorganism (for instance, pseudomones oleoverans). The Petri dishes are refrigerated for 24 hours and then placed in the drying cabinet for 18 hours at 30° C. Following incubation, the total diameter of the inhibition zones that emerged is measured.

| Tested Products | Amounts Deposited Per Disk | Inhibition Zone Diameter | Corresponding Amount of KATHON |
|---|---|---|---|
| B | 3.3 mg | 18 mm | 0 |
| B + $Cu^{++}$ 5% Cu $Cl_2$ | 3.3 mg | 18 mm | 0 |
| B + KATHON C.G. | 5 mg | 29 mm | 0.37 g |
| | 10 mg | 34 mm | 0.63 g |
| | 15 mg | 39 mm | 0.96 g |
| | 20 mg | 42 mm | 1.24 g |
| B + KATHON C.G. + $Cu^{++}$ 5% $CuCl_2$ | 5 mg | 28 mm | 0.33 g |
| | 10 mg | 34 mm | 0.63 g |
| | 15 mg | 38 mm | 0.88 g |
| | 20 mg | 40 mm | 1.05 g |

EXAMPLE 4

Measuring Odor Strength

A sample of persons undergoes the three test series below:
- determination of the concentration at the detection threshold (T.C.) of an odorous product (Steiger Chem. Tech., Vol 1, Apr. 1971),
- establishment of the reference curve using various samples containing multiples of the threshold concentration,
- determination of the activity of the bactericide by evaluating the odor strength stated in T.C. units.

The test of this example is carried out on a series of menstrual napkins containing the IRA A with 0.1 or 0.15% of KATHON C.G. and with 0.2% of $CuCl_2$ by weight with respect to the napkin. A control test also was carried out.

7 ml of beef blood is deposited per napkin plus 1 ml of a bacterial suspension which was prepared by mixing:
1 ml of a 24-hour culture of pseudomonas aeruginosa
1 ml of a 24-hour culture of escherichia coli
0.8 ml of a 48-hour culture of klebsiella pneumonia
5 ml of a 48-hour culture of proteus mirabilis Next, each napkin is placed in the polyethylene bottle, then made to incubate for 15 hours at 30° C. The measurement of the odor strength is made under the same conditions.

The following results are obtained:

| | |
|---|---|
| KATHON C.G. at 0.10% | 4 |
| KATHON C.G. at 0.15% | 1 |
| Control (no bactericides) | 6 |

EXAMPLE 5

Finished-Product Test

Diapers containing modified (5% of $Cu^{++}$ and 2% of KATHON) IRA B (AQUAKEEP) were worn for 12 hours by the incontinent. A control lot without modified IRA was tested in parallel. After 12 hours, olfactory measurement and pH measurement of the urine of the diaper were performed.

| Results: | Untreated IRA | Treated IRA |
|---|---|---|
| Number of tested diapers | 43 | 56 |
| Number of odorous diapers | 14 | 0 |
| Average pH | 8.5 | 7.3 |

Accordingly, the presence of bactericides on the IRA substantially decreases the appearance of malodorous products and restricts the increase in urine pH so as to reduce the urine's irritation powers.

I claim:

1. An absorbent article comprising a continuous material and a second material incorporated in said continuous material, said second material including a water-insoluble, hydrocolloidal polyelectrolyte capable of absorbing an aqueous liquid several times its own weight, said polyelectrolyte having an isothiazoline-one-3 derivative of the general formula:

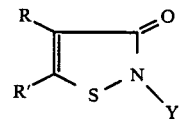

wherein
Y is a hydrogen atom, a $C_1$ to $C_8$ linear or branched alkyl group, or a $C_3$ to $C_6$ cycloalkyl group,
R is a hydrogen atom, a $C_1$ to $C_4$ alkyl group or a halogen, and
R' is a hydrogen atom, a $C_1$ to $C_4$ alkyl group or a halogen,
in contact therewith, said absorbent article being constructed and arranged for application to a human's anatomy for purposes of personal hygiene.

2. The article of claim 1 wherein said isothiazoline-one-3 derivative is a mixture of at least derivatives A and B and wherein in derivative A, R' is a halogen and in derivative B, R' is a hydrogen atom or a $C_1$ to $C_4$ alkyl group.

3. The article of claim 2 wherein said derivatives A and B have the structures -

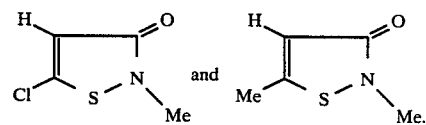

4. The article of claims 2 and 3 wherein the molar proportion of A/B is between 0.5 and 8.

5. The article of claim 1 wherein the isothiazoline-one-3 derivative is present in a proportion by weight of between about 1.5 and 750 ppm with respect to said polyelectrolyte.

6. The article of claim 5 wherein the isothiazoline-one-3 derivative is present in a proportion by weight of between about 7.5 and 450 ppm with respect to said polyelectrolyte.

7. The article of claim 1 wherein the isothiazoline-one-3 derivative is associated with the salt of a transition metal.

8. The article of claim 7 wherein the transition metal is selected from copper and zinc.

9. The article of claim 7 or claim 8 wherein the ratio by weight of the isothiazoline-one-3 derivative to the salt of a transition metal is between 0.012 and 0.018.

10. The article of claim 1 wherein the article is a diaper for babies or incontinent adults, or a menstrual napkin.

11. A process for forming said second material of claim 1 wherein said isothiazoline-one-3 derivative is added to a mixture of water/alcohol with proportions between 80/20 and 90/10, then the hydrocolloidal polyelectrolyte is added, followed by filitration.

12. The process of claim 11 wherein a salt of a transition metal is added before the hydrocolloidal polyelectrolyte is added.

* * * * *